(12) United States Patent
Thiry et al.

(10) Patent No.: US 9,409,991 B2
(45) Date of Patent: Aug. 9, 2016

(54) PHARMACEUTICAL COMPOSITIONS OF ANTIBODIES FOR TREATMENT OF DISEASES CAUSED BY INFLUENZA VIRUS

(75) Inventors: Michel Thiry, Trooz (BE); Andrey Martyushev-Poklad, Moscow (RU)

(73) Assignee: THERANOR SPRL (BE)

( * ) Notice: Subject to any disclaimer, the term of this patent is extended or adjusted under 35 U.S.C. 154(b) by 340 days.

(21) Appl. No.: 13/001,498

(22) PCT Filed: Jun. 26, 2009

(86) PCT No.: PCT/BE2009/000035
§ 371 (c)(1),
(2), (4) Date: Mar. 4, 2011

(87) PCT Pub. No.: WO2009/155670
PCT Pub. Date: Dec. 30, 2009

(65) Prior Publication Data
US 2011/0177081 A1    Jul. 21, 2011

(30) Foreign Application Priority Data
Jun. 27, 2008   (EP) .................................... 08447031

(51) Int. Cl.
*C07K 16/28* (2006.01)
*A61K 39/00* (2006.01)
*A61K 39/395* (2006.01)

(52) U.S. Cl.
CPC ............. *C07K 16/2896* (2013.01); *C07K 16/28* (2013.01); *C07K 16/2866* (2013.01); *A61K 39/3955* (2013.01); *A61K 2039/505* (2013.01); *C07K 2316/96* (2013.01); *C07K 2317/34* (2013.01)

(58) Field of Classification Search
CPC ............. A61K 2039/505; C07K 16/28; C07K 16/2866; C07K 16/2896; C07K 2317/34; C07K 2316/96
See application file for complete search history.

(56) References Cited

U.S. PATENT DOCUMENTS

| | | | |
|---|---|---|---|
| 6,287,853 B1 * | 9/2001 | Pestka et al. | 435/320.1 |
| 2004/0208874 A1 * | 10/2004 | Khare | 424/145.1 |
| 2005/0153910 A1 | 7/2005 | Matsumoto et al. | |
| 2006/0115475 A1 | 6/2006 | Carton et al. | |
| 2007/0098716 A1 | 5/2007 | Duffy et al. | |
| 2008/0317811 A1 * | 12/2008 | Andre et al. | 424/423 |
| 2009/0068684 A1 * | 3/2009 | Moritz et al. | 435/7.23 |

FOREIGN PATENT DOCUMENTS

| | | |
|---|---|---|
| EP | 1 295 606 | 3/2003 |
| WO | WO2006/054177 * | 5/2006 |

OTHER PUBLICATIONS

Schroder, M. et al. TLR3 in antiviral immunity: key player or bystander. Trends in Immunology, 2005, vol. 26, No. 9, p. 462-468.*
Edelmann, K.H. et al. Does toll-like receptor 3 play a biological role in virus infection. Virology, 2004, vol. 322, p. 231-238.*
International Search Report dated Aug. 20, 2010 in PCT/BE2009/000035 filed Jun. 26, 2009 (WO2009/155670).
International Preliminary Report on Patentability issued Jan. 5, 2011 in PCT/BE2009/000035 filed Jun. 26, 2009 (WO2009/155670).
Kenji Funami, et al., "The cytoplasmic 'linker region' in Toll-like receptor 3 controls receptor localization and signaling", International Immunology vol. 16, No. 8, Advance Access publication Jun. 28, 2004, copyright 2004 The Japanese Society for Immunology, pp. 1143-1154, cited in the Annex to EPO Form 2004, communication pursuant to Rule 71(3) EPC in priority EPO Application 08 447 031.9 filed Jun. 27, 2008.
"Homeopathy", Wikipedia article http://en.wikipedia.org/wiki/Homeopathy, printed Jul. 28, 2010, 28 pages, cited in the Annex to EPO Form 2004, communication pursuant to Rule 71(3) EPC in priority EPO Application 08 447 031.9 filed Jun. 27, 2008.
Chen, Keqiang, et al., "Toll-like receptors in inflammation, infection and cancer", International Immunopharmacology, Elsevier, Amsterdam, NL, vol. 7, No. 10, Jul. 31, 2007, pp. 1271-1285, XP022182172 ISSN: 1567-5769, cited in International Search Report mailed Feb. 8, 2010 of PCT/BE2009/00035 filed Jun. 26, 2009 (WO2009/155670).
Matsumoto, Misako et al., "Establishment of a monoclonal antibody against human Toll-like receptor 3 that blocks double-stranded RNA-mediated signaling", Biochemical and Biophysical Research Communications, Academic Press Inc., Orlando, Florida, U.S., vol. 293, No. 5, May 24, 2002, pp. 1364-1369, XP002974969 ISSN: 0006-291X, cited in International Search Report mailed Feb. 8, 2010 of PCT/BE2009/00035 filed Jun. 26, 2009 (WO2009/155670).
Duffy, Karen E., et al., "Down modulation of human TLR3 function by a monoclonal antibody", Cellular Immunology, Academic Press, San Diego, CA, U.S., vol. 248, No. 2, Dec. 26, 2007, pp. 103-114, XP022401829 ISSN: 0008-8749, cited in International Search Report mailed Feb. 8, 2010 of PCT/BE2009/00035 filed Jun. 26, 2009 (WO2009/155670).
Turner, Stephen J., et al., "Disregulated Influenza A Virus-Specific CD8+ T Cell Homeostasis in the Absence of Ifn-gamma signaling", Journal of Immunology, Baltimore, MD, vol. 178, No. 12, Jun. 15, 2007, pp. 7616-7622, XP002506551 ISSN: 0022-1767, cited in International Search Report mailed Feb. 8, 2010 of PCT/BE2009/00035 filed Jun. 26, 2009 (WO2009/155670).
Wood, Peter, Understanding Immunology: Second Edition, Pearson Education Limited, Essex, England, 2006.
Shih, Heather H., Discovery Process for Antibody-Based Therapeutics, Development of Antibody-Based Therapeutics, Chapter 2, M.A. Tabrizi et al (eds), 2012, pp. 9-32.

(Continued)

*Primary Examiner* — Robert Landsman
*Assistant Examiner* — Bruce D Hissong
(74) *Attorney, Agent, or Firm* — Hovey Williams LLP

(57) ABSTRACT

A pharmaceutical composition for prevention or treatment of viral infections including a formulation of full antibodies or fragments of antibodies specific to at least one of the following peptide sequences of toll-like receptor type 3: FYWNVSVHRVLGFKE (Seq ID NO:1), EYAAYIIHAYKD (Seq ID NO: 2), or to peptide sequence of interferon gamma receptor beta chain: LIKYWFHTPPSIPLQIEEYL (Seq ID NO: 3), or to peptide sequence of interferon gamma receptor alpha chain: SIILPKSLISW (Seq ID NO: 4).

15 Claims, No Drawings

(56) References Cited

OTHER PUBLICATIONS

Grewal, Iqbal S., Emerging Protein Biotherapeutics, CRC Press, Taylor & Francis Group, Boca Raton, FL, 2009.

Dessain, Scott K., Human Antibody Therapeutics for Viral Disease, Current Topics in Microbiology and Immunology, vol. 317, Springer, 2008, 51-53.

Moroney et al., Modern Antibody Technology: The Impact on Drug Development, Chapter 2, Modern Biopharmaceuticals: Design, Development and Optimization, Edited by J. Knablein, Wiley-VCH, 2005.

Rydzewski, Robert M., Real World Drug Discovery a Chemist's Guide to Biotech and Pharmaceutical Research, Chapter 5, 2008, Elsevier Ltd., 193-194.

* cited by examiner

```
                      SEQUENCE LISTING

<160> NUMBER OF SEQ ID NOS: 10

<210> SEQ ID NO 1
<211> LENGTH: 15
<212> TYPE: PRT
<213> ORGANISM: homo sapiens
<220> FEATURE:
<221> NAME/KEY: MISC_FEATURE
<222> LOCATION: <1or > 15
<223> OTHER INFORMATION: /note="before/after the sequence, we can find
      the (NH2) radical / the (COOH) radical

<400> SEQUENCE: 1

Phe Tyr Trp Asn Val Ser Val His Arg Val Leu Gly Phe Lys Glu
1               5                   10                  15

<210> SEQ ID NO 2
<211> LENGTH: 12
<212> TYPE: PRT
<213> ORGANISM: homo sapiens
<220> FEATURE:
<221> NAME/KEY: MISC_FEATURE
<222> LOCATION: <1or > 12
<223> OTHER INFORMATION: /note="before/after the sequence, we can find
      the (NH2) radical / the (COOH) radical

<400> SEQUENCE: 2

Glu Tyr Ala Ala Tyr Ile Ile His Ala Tyr Lys Asp
1               5                   10

<210> SEQ ID NO 3
<211> LENGTH: 20
<212> TYPE: PRT
<213> ORGANISM: homo sapiens
<220> FEATURE:
<221> NAME/KEY: MISC_FEATURE
<222> LOCATION: <1or > 16
<223> OTHER INFORMATION: /note="before/after the sequence, we can find
      the (NH2) radical / the (COOH) radical

<400> SEQUENCE: 3

Leu Ile Lys Tyr Trp Phe His Thr Pro Pro Ser Ile Pro Leu Gln Ile
1               5                   10                  15

Glu Glu Tyr Leu
            20

<210> SEQ ID NO 4
<211> LENGTH: 12
<212> TYPE: PRT
<213> ORGANISM: homo sapiens
```

-continued

```
<220> FEATURE:
<221> NAME/KEY: MISC_FEATURE
<222> LOCATION: <1or > 12
<223> OTHER INFORMATION: /note="before/after the sequence, we can find
      the (NH2) radical / the (COOH) radical

<400> SEQUENCE: 4

Ser Ile Ile Leu Pro Lys Ser Leu Ile Ser Val Val
1               5                   10

<210> SEQ ID NO 5
<211> LENGTH: 15
<212> TYPE: PRT
<213> ORGANISM: Mus
<220> FEATURE:
<221> NAME/KEY: MISC_FEATURE
<222> LOCATION: <1or > 15
<223> OTHER INFORMATION: /note="before/after the sequence, we can find
      the (NH2) radical / the (COOH) radical

<400> SEQUENCE: 5

Phe Tyr Trp Asn Val Ser Val His Arg Ile Leu Gly Phe Lys Glu
1               5                   10                  15

<210> SEQ ID NO 6
<211> LENGTH: 12
<212> TYPE: PRT
<213> ORGANISM: Mus
<220> FEATURE:
<221> NAME/KEY: MISC_FEATURE
<222> LOCATION: <1or > 12
<223> OTHER INFORMATION: /note="before/after the sequence, we can find
      the (NH2) radical / the (COOH) radical

<400> SEQUENCE: 6

Glu Tyr Thr Ala Tyr Ile Ile His Ala His Lys Asp
1               5                   10

<210> SEQ ID NO 7
<211> LENGTH: 18
<212> TYPE: PRT
<213> ORGANISM: Mus
<220> FEATURE:
<221> NAME/KEY: MISC_FEATURE
<222> LOCATION: <1or > 18
<223> OTHER INFORMATION: /note="before/after the sequence, we can find
      the (NH2) radical / the (COOH) radical

<400> SEQUENCE: 7

Lys Tyr Trp Phe Gln Ala Pro Pro Asn Ile Pro Glu Gln Ile Glu Glu
1               5                   10                  15

Tyr Leu

<210> SEQ ID NO 8
<211> LENGTH: 12
<212> TYPE: PRT
<213> ORGANISM: Mus
<220> FEATURE:
<221> NAME/KEY: MISC_FEATURE
<222> LOCATION: <1or > 12
<223> OTHER INFORMATION: /note="before/after the sequence, we can find
      the (NH2) radical / the (COOH) radical

<400> SEQUENCE: 8

Ser Ile Met Leu Pro Lys Ser Leu Leu Ser Val Val
1               5                   10

<210> SEQ ID NO 9
```

```
<211> LENGTH: 13
<212> TYPE: PRT
<213> ORGANISM: Mus
<220> FEATURE:
<221> NAME/KEY: MISC_FEATURE
<222> LOCATION: <1or > 13
<223> OTHER INFORMATION: /note="before/after the sequence, we can find
      the (NH2) radical / the (COOH) radical

<400> SEQUENCE: 9

Met Ala Ser Gly Tyr Asp Lys Pro His Met Leu Val Asp
1               5                   10

<210> SEQ ID NO 10
<211> LENGTH: 12
<212> TYPE: PRT
<213> ORGANISM: Mus
<220> FEATURE:
<221> NAME/KEY: MISC_FEATURE
<222> LOCATION: <1or > 12
<223> OTHER INFORMATION: /note="before/after the sequence, we can find
      the (NH2) radical / the (COOH) radical

<400> SEQUENCE: 10

Leu Glu Glu Arg Asp Phe Glu Ala Gly Val Leu Val
1               5                   10
```

PHARMACEUTICAL COMPOSITIONS OF ANTIBODIES FOR TREATMENT OF DISEASES CAUSED BY INFLUENZA VIRUS

CROSS-REFERENCE TO RELATED APPLICATIONS

This application is the National Stage of International Application No. PCT/BE2009/000035, filed Jun. 26, 2009, which claims the priority benefit of European Application No. 08447031.9, filed Jun. 27, 2008, the disclosures of which are incorporated by reference herein in their entirety.

SEQUENCE LISTING

The following application contains a sequence listing in computer readable format (CRF), submitted as a text file in ASCII format entitled "42580.txt" created on Dec. 22, 2010, as 4 KB. The contents of the CRF are hereby incorporated by reference herein.

TECHNICAL FIELD

The present invention relates to the treatment and prevention of diseases caused by viruses, including viral infections. More particularly, this invention concerns novel therapeutic agents designed to modulate the antiviral host response and to reduce the severity and duration of viral infections and complications of viral infections.

BACKGROUND ART

There are several basic approaches to combat viral infections (apart from the treatment of individual symptoms): (1) vaccination—induction of immunity to prevent viral infection, (2) targeting viral replication cycle with small molecule agents or therapeutic antibodies, and (3) activation of host response (primarily, with the use of interferons or interferon inducers) WAGNER, E. K., et al. Basic Virology. 2nd edition. Oxford: Blackwell Publishing, 2004. ISBN 1405103469. p. 96-116.

Each of the mentioned approaches has certain limitations or disadvantages. Vaccination is only expedient for vaccine-preventable infections; natural variability of the pathogen (e.g., influenza virus) can minimize the efficacy of vaccination; finally, vaccination is infrequently associated with undesirable reactions. Each therapeutic agent targeting viral replication cycle is effective in only a narrow range of disease conditions caused by pathogens sharing common molecular target; the use of such agents can be associated with the development of resistance and/or undesirable reactions. It is also very important to take into consideration that severity and duration of the conditions caused by viruses depend on two groups of factors: virus concentrations in the target organs (with corresponding direct cytopathic effect) linked with the rate of viral clearance on the one hand and adequacy of host innate and adaptive immune response on the other hand. Thus, even a relatively low dose of a highly pathogenic virus can cause a very severe disease, the severity being often the result of 'cytokine storm' (SZRETTER, K. J., et al. Role of host cytokine responses in the pathogenesis of avian H5N1 influenza viruses in mice. *J Virol.* 2007, vol. 81, no. 6, p. 2736-44.) caused by a kind of inopportune reaction of the host defence.

The agents capable of activating the host response (biological response modifiers, immunomodulators) seem to be a promising group of antiviral therapeutics with regard to their 'natural' mode of action and independence on the particular cause of viral infection. This group of therapeutics can be exemplified by interferons (e.g., pegylated interferon alpha-2a), imiquimod (interferon inducer acting as an agonist of toll-like receptor 7), tilorone (orally active interferon inducer). However, all known interferon preparations have significant adverse effects, and synthetic interferon inducers have either problems of safety or bioavailability.

There are numerous therapeutic agents comprising full antibodies or antibody fragments designed for the treatment of different diseases (Brekke O H, Sandlie I. Therapeutic antibodies for human diseases at the dawn of the twenty-first century. Nat Rev Drug Discov. 2003 January; 2(1):52-62.). Several of them are designed for diseases caused by viruses: for example, in HIV infection, antibody fragments are proposed to block a viral protein gp120 (Danishefsky et al., US patent application 20060229432, published Oct. 12, 2006); in respiratory syncytial virus (RSV) infection monoclonal antibodies are known (palivizumab) to target RSV, prevent, treat or ameliorate symptoms associated with an RSV infection. The mentioned agents are intended to block/inhibit their target molecule, they are administered in substantial doses (at least 0.001 mg/kg). Theoretically, the prior art includes oral administration, but the existing products cannot be used in oral dosage forms due to poor bioavailability provided by this route for protein based medicine. Less numerous peroral pharmaceutical formulations based on antibodies or antibody fragments (US patent applications 20060002927 (10513109), 20050136103 (10942300), 20030153022 (10287821), etc.) target a molecule within gastrointestinal tract or a bacterial exogenous peptide, and are administered in substantial doses essential to achieve certain concentration in the gastrointestinal tract and block their target Apart from antiviral agents, prior art covers mostly antibodies aimed at molecular targets that are up-regulated in a particular disease condition with the intention of lowering their level to normality. An example closest to the subject of the present application is the US patent application US20060115475 by Carton et al., "Toll like receptor 3 antagonists, methods and uses". It discloses anti-TLR3 (Toll like receptor type 3) antibodies effective in the treatment and prevention of inflammatory conditions, including those associated with infections, by antagonizing TLR3 to inhibit cellular production of pro-inflammatory cytokines. As can be concluded from description of that application, the authors propose to use monoclonal antibodies directed to one of the numerous epitopes of extracellular ligand-binding domain of TLR3 which has the length of 703 amino acids. These antibodies are injected intraperitoneally after a sub-lethal influenza infection, shortly before (prophylactic injection) and shortly after (therapeutic injection) a challenge with *S. pneumoniae*, in order to prevent septic shock caused by the bacterial pathogen on the background of a subsided influenza infection. Therefore, the US20060115475 application rather focuses on prevention and treatment of lethal inflammatory complications of bacterial infections by antagonizing extracellular domain of TLR3, than demonstrates any prophylactic or therapeutic use of anti-TLR3 antibodies in a viral infection.

Another general approach is the use of antibodies or antibody fragments to target markers specifically expressed by malignant or otherwise diseased cells. Mimetics (receptor agonists) based on antibodies are known in prior art, but none of them is actually used in practice.

In addition to the above-mentioned antiviral approaches and numerous symptomatic therapeutics for viral infections, there are several homeopathic medicinal agents registered for prevention and treatment of viral infections, primarily influenza and common cold. Most of them are individually prescribed by doctor on the basis of patient specific symptoms according to the homeopathic tradition. However, several products claim universal indications to be effective in upper respiratory infections. Most noteworthy of them are Oscillococcinum (marketed in France, several other EU states and North America) and Anaferon (marketed in Russia and several neighbouring states, but not in the EU). Oscillococcinum is made from heart and liver of duck (homoeopathic dilution K200), Anaferon is made from antibodies to interferon gamma (mixture of homeopathic dilutions (RU WO2005000350 A (EPSHTEIN OI) 6 Jan. 2005). Whereas homeopathic therapeutics are generally recognized as safe, the efficacy of the mentioned products remains uncertain, at least, judging from the published studies. For Oscillococcinum there is no published evidence of efficacy in animal models of viral infections, and its clinical benefit in the treatment of influenza and influenza-like syndrome is regarded as very moderate (VICKERS, A. J., et al. Homoeopathic Oscillococcinum for preventing and treating influenza and influenza-like syndromes. *Cochrane Database Syst Rev.* 2006 July, vol. 19, no. 3, p.CD001957.). For Anaferon, animal efficacy data is published (SERGEEV, A. N., et al. [Antiviral activity of oral ultralow doses of antibodies to gamma-interferon: experimental study of influenza infection in mice]. *Antibiot Khimioter.* 2004, vol. 49, no. 11, p. 7-11.; SUSLOPAROV, M. A., et al. [Efficacy of therapeutic and prophylactic actions of ultralow doses of antibodies to gamma-interferon in experimental murine model of herpes virus]. *Antibiot Khimioter.* 2004, vol. 49, no. 10, p. 3-6.); the benefits of the product in human clinical trials can only be estimated from abstracts of scientific conferences.

A general approach was proposed for manufacturing homeopathic products using "antibodies to an antigen acting as a direct cause of a pathological syndrome or involved in regulation of mechanisms of its formation" (EP1295606 A (EPSHTEIN O. I.) 26 Mar. 2003). But the cited patent application does not suggest any clue to choosing particular molecular target in a particular disease. When one considers that hundreds of proteins are involved in the regulation of host defence against viral infections (each of the proteins including dozens of epitopes to raise antibodies to), one has to select the best drug candidate out of thousands of possible options.

DISCLOSURE OF INVENTION

The present invention is aimed at developing an effective and safe medicinal product which could act as an immunomodulator, activating and modulating host response to a broad range of viral pathogens, thus providing prophylactic and therapeutic benefits in a wide range of diseases caused by viruses.

Technical Problem

Viral infections and diseases caused by viruses in general present a generally unmet medical need: the available therapeutics with confirmed efficacy are either effective in only very narrow range of infections, or they have an unfavourable safety profile, or they tend to loose efficacy due to viral resistance.

Technical Solution

The technical problem of designing a pharmaceutical composition effective and safe in a broad range of viral infections is solved by incorporating in the said composition an effective therapeutic amount or formulation of full antibodies or antigen-binding fragments of antibodies specific to at least one peptide sequence, selected from the group consisting of the following sequences: toll-like receptor type 3 sequence (NH2)FYWNVSVHRVLGFKE(COOH) [FYW h, Seq ID NO: 1], toll-like receptor type 3 sequence (NH2)EYAAYIIHAYKD(COOH) [EYA h, Seq ID NO: 2], interferon gamma receptor beta chain sequence (NH2)LIKYWFHTPPSIPLQIEEYL(COOH) [LIK h, Seq ID NO: 3], interferon gamma receptor alpha chain sequence (NH2)SIILPKSLISW(COOH) [SII h, Seq ID NO: 4], or an effective therapeutic amount of a mixture comprising: (a) at least one or more full antibodies or antigen-binding fragments of antibodies specific to a first peptide sequence selected from the group consisting of the following sequences: toll-like receptor type 3 sequence (NH2)FYWNVSVHRVLGFKE(COOH) [FYW h, Seq ID NO: 1], toll-like receptor type 3 sequence (NH2)EYAAYIIHAYKD(COOH) [EYA h, Seq ID NO: 2], interferon gamma receptor beta chain sequence (NH2)LIKYWFHTPPSIPLQIEEYL(COOH) [LIK h, Seq ID NO: 3], interferon gamma receptor alpha chain sequence (NH2)SIILPKSLISW(COOH) [SII h, Seq ID NO: 4], and (b) at least one or more full antibodies or antigen-binding fragments of antibodies specific to a second peptide sequence selected from the group consisting of the following sequences: toll-like receptor type 3 sequence (NH2)FYWNVSVHRVLGFKE(COOH) [FYW h, Seq ID NO: 1], toll-like receptor type 3 sequence (NH2)EYAAYIIHAYKD(COOH) [EYA h, Seq ID NO: 2], interferon gamma receptor beta chain sequence (NH2)LIKYWFHTPPSIPLQIEEYL(COOH) [LIK h, Seq ID NO: 3], interferon gamma receptor alpha chain sequence (NH2)SIILPKSLISW(COOH) [SII h, Seq ID NO: 4], whereby said second peptide sequence is different from said first peptide sequence.

The invention relates to such a pharmaceutical composition for the treatment or prevention of a disease caused by a virus or a mixture of different viruses, in vertebrate animals and humans, especially in humans.

In another embodiment of the invention, the described pharmaceutical composition is used as a medicament intended for enteral, parenteral, oral, peroral, peritoneal or topical administration.

The pharmaceutical composition according to the present invention may be used for a disease caused by any known or emerging virus and in particular virus selected from the group consisting of: Adenoviruses; Caliciviruses (in particular, Norovirus); Coronaviruses; Coxsackieviruses; Epstein-Barr virus; Flaviviruses (in particular, West Nile virus, dengue virus, tick-borne encephalitis virus, yellow fever virus); Hepatitis A virus; Hepatitis B virus; Hepatitis C virus; Herpes simplex viruses types 1, 2, and 8; Cytomegalovirus; Human immunodeficiency virus (HIV); Influenza viruses; Measles virus; Human metapneumovirus; Mumps virus; Human papillomavirus; Parainfluenzavirus; Poliovirus; Rabies virus; Respiratory syncytial virus; *Rhinoviruses*; Rotavirus; Rubella virus; *Varicella-zoster* virus.

In one of the embodiments, the pharmaceutical composition contains an effective therapeutic amount of homeopathic formulation prepared with the use of technology comprising multiple cycles of consecutive dilution and vertical shaking—in particular, by the methods of manufacturing described in Homeopathic pharmacopoeia.

Alternatively, in designing the pharmaceutical composition a target peptide may be used which has amino acid sequence at least 70% identical or 85% similar to at least one of the listed amino acid sequences of toll-like receptor type 3 or interferon gamma receptor.

In another embodiment of the invention, the used antibody fragments are Fab, F(ab)2 fragments, or antibody monomers containing one heavy and one light immunoglobulin chain. Antibody fragments according to the present invention may be obtained by treating whole antibodies with an endopeptidase such as papain, pepsin, or ficin, and also be manufactured by the methods of genetic engineering.

In one of the embodiments of the invention, formulation in the pharmaceutical composition may be represented by a homeopathic dilution (potency) or a mixture of several homeopathic dilutions (potencies) designed for oral administration.

In another embodiment of the invention, the pharmaceutical composition comprises a mixture of full antibodies or fragments of antibodies raised to two or three of the mentioned peptides.

In designing the pharmaceutical agent according to the present invention, in case the agent is designed for a vertebrate other than a human, the targeted peptide sequence may be corrected for species specificity.

In one of the embodiments of the invention, a method for preparation of the pharmaceutical composition is disclosed, which comprises at least the following steps, advantageously combined with one or more classical virus reduction steps like acid treatment, nanofiltration or UV light exposure:

1) Peptide synthesis,
2) Coupling with Keyhole Limpet Haemocyanin,
3) Immunization of an animal with peptide-KLH conjugate,
4) Collection and preliminary purification of immune sera,
5) Affinity purification on protein A,
6) Purification on KLH-BrCN-Sepharose or affinity purification on the peptide,
7) Optional purification by ion exchange chromatography
8) Possibly repeated consecutive dilution and potentisation according to technology described in Homeopathic pharmacopoeia,
9) Preparation of either liquid or solid dosage form.

The method can comprise one or more further steps, such as adding one or more excipients, granulating steps, tabletting steps, etc. In case of consecutive dilution and potentisation according to technology described in Homeopathic Pharmacopoeia, the most effective potency or combination of potencies is chosen through routine screening.

Advantageous Effects of the Invention

Owing to its mode of action involving modulation of innate and adaptive host response to viruses, the pharmaceutical composition designed according to the present invention enables effective and safe treatment or prevention of a wide range of conditions caused by viruses, basically regardless of the exact virus type responsible for the disease, which is currently impossible with the use of other therapeutics.

DEFINITIONS

The term "Antibody" as used herein refers to a monoclonal or polyclonal antibody (immunoglobulin) molecule. The term "antigen-binding fragment" of a full length antibody (or simply "antibody portion," or "fragment"), as used herein, refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab').sub.2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) Science 242:423-426; and Huston et al. (1988) Proc. Natl. Acad. Sci. USA 85:5879-5883. Optionally, according to the present invention, antibodies are IgG antibodies, particularly IgG1. F(ab')2 refers the antibody fragment obtainable after pepsin cleavage and is built up of both light chains and parts of the heavy chains disulfide linked via the hinge region. The Fab fragment is obtainable from the intact antibody or from the F(ab')2 by papain digestion of the hinge region and contains a one light chain and one part of the heavy chain. Fragments of antibodies can also be obtained by synthesis or by recombinant methods described in the art.

"Antibody specificity" is an intrinsic property of antibodies, which characterizes their ability to bind the corresponding epitope of the corresponding antigen with high affinity (association) constant (Ka). Ka for antibodies which can be regarded specific to a particular antigen lies within the range of $10^5$ to $10^{10}$ $M^{-1}$. (Foote J, Eisen H N. Kinetic and affinity limits on antibodies produced during immune responses. Proc Natl Acad Sci USA. 1995 Feb. 28; 92(5):1254-6.). Ka may be measured by equilibrium dialysis or Biacore technology both for monoclonal antibodies, and for polyclonal antibodies where the average Ka of the mixture is considered (Murphy K M, Travers P, Walport M. Janeway's Immunobiology. $5^{th}$ edition. Garland Science Textbooks, 2001, Appendix I, paragraph A-9, FIGURE A.11).

"Similarity of peptide sequence". Comparisons of protein sequences are designated in terms of sequence identity or sequence similarity. Where in accordance with the present invention comparisons are made between amino acid sequences of the target peptides, the level of sequence identity or similarity between two sequences may include having at least 70%, preferably at least 80% more preferably at least 90%, even more preferably at least 95% and most preferably at least 99% sequence identity or similarity between two sequences. Amino acid sequences which are "identical" means that when two sequences are aligned, the percent sequence identity, i.e. the number of positions with identical amino acids divided by the number of amino acids in the shorter of the sequences, is higher than 70%, preferably at least 90%, even more preferably at least 95%, most preferably at least 99%. The alignment and comparison of two amino acid sequences are made with the use of BLAST algorithm described by Altschul et al. (1997) (Altschul S. F., Madden T. L., Schäffer A. A., Zhang J., Zhang Z., Miller W., Lipman D. J. Gapped BLAST and PSI-BLAST: a new generation of protein database search programs. Nucleic Acids Res. 25:3389-3402 (1997).)

Routes of administration of the pharmaceutical composition according to the present invention encompass either enteral (any form of administration that involves any part of the gastrointestinal tract from mouth to anus, such as oral, peroral, etc.), parenteral (by injection, infusion, transmucosal, transdermal, or inhalational application), or topical routes.

"Formulation" in the instant invention means "the product of a process by which a drug substance is combined with different chemical substances to produce a medicinal product"

"Homeopathic technology", or "methods of manufacturing described in Homeopathic pharmacopoeia", encompass all techniques and methods adopted in the practice of manufacturing homeopathic medicinal products, for example, described in detail in German Homoeopathic Pharmacopoeia (GHP, Homoopathisches Arzneibuch), Translation of the 5$^{th}$ Supplement (1991) to the 1978 edition, Deutscher Apotheker-Verlag Stuttgart, pp. 27-82) or any other national Homeopathic Pharmacopoeia of the EU states or of the USA. Homeopathic technology for liquid dosage forms generally includes exposure of the starting substance (also called 'stock', or 'mother tincture') to repeated cycles of diluting with alcohol or water and then vigorous shaking by at least ten hard strikes against an elastic body, this process also being called "potentisation", "dynamisation", or "succussion". Solutions produced by such method are called 'homeopathic dilutions', or 'potencies'. Three potency scales are in regular use in homeopathy: the centesimal or "C scale", where a substance is diluted by a factor of 100 at each stage; decimal or "X scale", where a substance is diluted by a factor of 10 at each stage; and "LM scale", where a substance is diluted by a factor of 50000 at each stage. Dilution may take place in a new vessel for each new potency (traditional approach), or in the same glass vessel after 99% of the previous dilution is discarded (so-called Korsakovian dilutions which are sometime abbreviated K or "K scale"). Generally homeopathic potencies below C12 are called low dilutions', C12 and C30—'medium dilutions', above C30—'high dilutions'.

BEST MODE FOR CARRYING OUT THE INVENTION

The best mode of carrying out the present invention is illustrated in examples below.

EXAMPLE 1

Preparation of the Pharmaceutical Composition

The manufacturing process includes the following basic steps, adventitious agents inactivation and removal steps are not mentioned:
1) Peptide synthesis.
2) Coupling with KLH.
3) Immunization of rabbits with peptide-KLH conjugate.
4) Collection and preliminary purification of immune sera (ammonium sulphate precipitation).
5) Protein A purification to remove non-IgG proteins.
6) Purification on KLH-BrCN-Sepharose to remove anti-KLH antibodies. Alternatively, at this step affinity purification on the target peptide may be performed As well as an additional ion exchange chromatography
7) Fragmentation (either by using endopeptidase, with subsequent removal of Fc portions—to produce Fab, F(ab)2 fragments, or by reduction and S-alkylation of interheavy-chain disulfide bonds—to produce antibody halves). Step 7 is optional.
8) Possibly, dilution and potentisation by one of the methods laid down in one of existing Homeopathic Pharmacopoeias (German, French, European, British, US, Indian).
9) Preparation of either liquid or solid dosage form according to the Homeopathic Pharmacopoeia.

The so prepared pharmaceutical compositions contain an effective therapeutic amount or quantity of one or more full polyclonal rabbit antibodies and Fab fragments of antibodies to one or more peptides selected from the group consisting of:
toll-like receptor type 3 sequence (NH2)FYWNVSVHRV-LGFKE(COOH) [FYW h, Seq ID NO: 1], toll-like receptor type 3 sequence (NH2)EYAAYIIHAYKD(COOH) [EYA h, Seq ID NO: 2],
interferon gamma receptor beta chain sequence (NH2) LIKYWFHTPPSIPLQIEEYL(COOH) [LIK h, Seq ID NO: 3],
interferon gamma receptor alpha chain sequence (NH2) SIILPKSLISW(COOH) [SII h, Seq ID NO: 4], and
5) mixtures thereof.

EXAMPLE 2

The Efficacy of the Pharmaceutical Compositions in an Animal Model of Viral Infection The efficacy of pharmaceutical compositions according to the invention based on specific antibodies and antibody fragments was evaluated in murine influenza host resistance model, and compared with the efficacy of compositions not according to the invention.

The following starting substances (mouse counterparts of the respective human target peptides were used for raising the antibodies) were tested, after being diluted with water in accordance with homeopathic technology; concentration of the active agent in the water solution formulation was below 0.1%: Full polyclonal rabbit antibodies and Fab fragments of antibodies to peptides 1) FYWNVSVHRILGFKE ('FYW') from Toll like receptor 3 (invention) (FYW m, SEQ NO: 5);

2) EYTAYIIHAHKD ('EYT') from Toll like receptor 3 (invention) (EYT m, Seq ID NO: 6);

3) KYWFQAPPNIPEQIEEYL ('KYW') interferon gamma receptor 2 (invention) (KYW m, Seq ID NO: 7);

4) SIMLPKSLLSW ('SIM') from interferon gamma receptor 1 (invention) (SIM m, Seq ID NO: 8);

5) MASGYDKPHMLVD ('MAS') from interferon gamma receptor 1 (not according to the invention) (MAS, Seq ID NO: 9);

6) LEERDFEAGVLG ('LEE') from Toll like receptor 3 (not according to the invention) (LEE, Seq ID NO: 10);

7) Full polyclonal rabbit antibodies to mouse interferon gamma (IFNg) (not according to the invention);

8) Rabbit preimmune serum (negative control).

The agents were diluted 1:2 in drinking water and given in free access for 5 days before and for 10 days after viral challenge to Balb/c female mice (8 weeks old, 14-20 g). The mice of positive control group received two intranasal doses of Recombinant Mouse Interferon Alpha (IFNa), $4\times10^3$ U/mouse, 2× (24 hours and 4 hours prior to infection).

On day 0 the animals were anesthetized with isoflurane and infected intranasally with mouse-adapted influenza virus as a $10^{-2}$ dilution of the stock virus (approximately $4\times10^4$ plaque forming units) in a volume of 50 mcL (50 microlitre).

Starting on the day before viral challenge, body weight and clinical state were evaluated daily for each mouse. Clinical observation scores were 0 (healthy), 1 (slightly ruffled fur), 2 (ruffled fur), 3 (ruffled fur/hunched posture), 4 (moribund/dead).

The efficacy of the tested agents was judged by the following endpoints: (1) Duration of clinical infection (number of days with clinical observation score >0); (2) Overall severity of clinical infection (sum of clinical scores over the followon). Statistical significance of the differences across all tested groups was evaluated by ANOVA, and Turkey test was used to assess paired inter-group differences. ANOVA for both endpoints showed that the difference in results across the groups was statistically significant. Detailed results are listed in the Table 1 below.

TABLE 1

| Group (n) | Disease duration, days (M ± SEM) | P value vs negative control | Disease severity, score (M ± SEM) | P value vs negative control |
|---|---|---|---|---|
| Negative control (40) | 5.93 ± 0.11 | — | 8.05 ± 0.29 | — |
| IFNa (20) | 4.60 ± 0.23 | <0.001 | 4.80 ± 0.23 | <0.001 |
| FYW full Ab* (20) | 5.25 ± 0.13 | 0.002 | 6.35 ± 0.44 | 0.01 |
| FYW Fab (20) | 5.15 ± 0.08 | <0.001 | 7.15 ± 0.37 | 0.648 |
| EYT full Ab (20) | 5.40 ± 0.12 | 0.051 | 6.65 ± 0.36 | 0.08 |
| EYT Fab (20) | 5.35 ± 0.13 | 0.016 | 7.10 ± 0.45 | 0.572 |
| KYW full Ab (20) | 5.35 ± 0.11 | 0.019 | 7.15 ± 0.37 | 0.648 |
| SIM full Ab (20) | 5.25 ± 0.10 | 0.002 | 6.60 ± 0.34 | 0.058 |
| IFNg full Ab (20) | 5.45 ± 0.12 | 0.118 | 7.90 ± 0.42 | 0.999 |
| LEE full Ab (20) | 6.10 ± 0.07 | — | 8.60 ± 0.20 | — |
| MAS full Ab (20) | 5.40 ± 0.14 | >0.05 | 7.30 ± 0.42 | >0.05 |

*Ab stands for 'antibodies'.

The findings demonstrate that, quite unexpectedly, the use of full antibodies and Fab fragments of antibodies to several target peptides (FYW, EYT, KYW, and SIM) already in the form of highly diluted compositions can produce a significant reduction of severity and/or duration of clinical infection in influenza host resistance model in mice (moderate influenza, with body weight loss >10%), which most closely reproduces the corresponding human disease.

The choice of correct peptide target for antibodies appears to be crucial for the efficacy, as neither the product covered by WO2005000350 A (EPSHTEIN O I) 6 Jan. 2005 and also mentioned in EP1295606 A (EPSHTEIN O. I.) 26 Mar. 2003, nor full antibodies or antibody fragments directed to LEE and MAS peptides showed any significant therapeutic effect in the model.

The findings for mouses with the treatment with compositions according to the invention can be extrapolated to treatment of human, for treating or preventing disease caused by a virus or a mixture of viruses, especially human resistant viruses.

EXAMPLE 3

The Efficacy of Different Routes of Administration

The efficacy of pharmaceutical compositions based on antibodies used with two different administration routes was evaluated in murine influenza host resistance model.

The following samples were tested (designation of peptide target as in Example 2):

Sample 1. Full antibodies to FYW peptide, diluted with saline solution. This formulation was administered in two intraperitoneal injections (10 ng/kg each): 24 hours before and 24 hours after viral challenge.

Sample 2. Full antibodies to FYW peptide, diluted with saline solution, concentration 10 ng/mL. This formulation was given intranasally, 0.05 mL (0.5 ng)/mouse, twice daily, for 5 days before and for 10 days after viral challenge.

Sample 3. Rabbit preimmune serum (negative control), formulated and administered as Sample 1.

Sample 4. Rabbit preimmune serum (negative control), formulated and administered as Sample 2.

The mice of positive control group received two intranasal doses of Recombinant Mouse Interferon Alpha (IFNa), $4 \times 10^3$ U/mouse, 2× (24 hours and 4 hours prior to infection).

Balb/c female mice (8 weeks old, 14-20 g) were anesthetized with isoflurane and infected intranasally with mouse-adapted influenza virus as a $10^{-2}$ dilution of the stock virus (approximately $4 \times 10^4$ plaque forming units) in a volume of 50 mcL.

The clinical course of infection was monitored daily, the same scoring and endpoints being used as in Example 2. Detailed results are listed in the Table 2 below.

TABLE 2

| Group (n) | Disease duration, days (M ± SEM) | P value vs corresponding negative control | Disease severity, score (M ± SEM) | P value vs negative control |
|---|---|---|---|---|
| Negative control - sample 3 (20) | 5.98 ± 0.10 | — | 8.08 ± 0.21 | — |
| Negative control - sample 4 (20) | 6.04 ± 0.15 | — | 8.25 ± 0.32 | — |
| IFNa (20) | 4.65 ± 0.21 | <0.001 | 4.83 ± 0.20 | <0.001 |
| Intraperitoneal FYW full Ab - sample 1 (20) | 5.20 ± 0.15 | 0.002 | 6.31 ± 0.41 | 0.01 |
| Intranasal FYW full Ab - sample 2 (20) | 5.26 ± 0.17 | 0.005 | 6.37 ± 0.44 | 0.01 |

The findings show that full antibodies to a specific TLR3 peptide with both intraperitoneal route (in the dose of 10 ng/kg) and intranasal formulation (in the dose of 0.5 ng/mouse) are effective in the treatment of non-lethal influenza in mice.

The efficiency of the composition of the invention was also observed with higher therapeutic doses.

MODE(S) FOR CARRYING OUT THE INVENTION

The use of highly diluted compositions (possibly in the form of homeopathic composition) of full antibodies to the peptides are not the sole mode for carrying out the invention, however, the obvious advantages of this approach are cost efficiency (due to relative simplicity of manufacturing and economy of the starting substance) and safety intrinsic to the resulting medicinal product intended for oral administration.

Alternatively to the mode for carrying out the invention described in the examples above, antibody fragments can be obtained by the methods of genetic engineering. Also therapeutic agent may include antibodies or antibody fragments raised to two, three or four of the best target peptides simultaneously. Alternatively, a mixture of several highly diluted compositions (possibly homeopathic potencies) of antibodies or antibody fragments may be used in one therapeutic agent/composition and/or in one therapeutic treatment, for example for administering one active agent and thereafter another active agent. As illustrated in examples, in the treatment of different species of animals, species specificity of the target peptide(s) may be taken into account. The use of highly diluted compositions (possibly homeopathic dosage forms) other than oral is also possible.

As the molecular targets for the therapeutics agents according to the present invention represent universal regulatory molecules involved in innate and adaptive host response to viral infections, the pharmaceutical agents in accordance with the present invention can be used in diseases caused by known or emerging viruses other than influenza virus, and also those caused by a mixture of different viruses, chosen from but not limited to the following list: Adenoviruses; Coronavirus; Coxsackieviruses; Epstein-Barr virus; Flaviviruses (West Nile virus, dengue virus, tick-borne encephalitis virus, yellow fever virus); Hepatitis A virus; Hepatitis B virus; Hepatitis C virus (a flavivirus); Herpes simplex virus, types 1, 2, 8; Cytomegalovirus; Human immunodeficiency virus (HIV); Influenza viruses; Measles virus; Human metapneumovirus; Mumps virus; Norovirus (and other caliciviruses); Human papillomavirus; Parainfluenzavirus; Poliovirus; Rabies virus; Respiratory syncytial virus; *Rhinoviruses* (the major cause of common cold); Rotavirus; Rubella virus; *Varicella-zoster* virus.

Dosage schedule may be selected or adjusted depending on the selected pharmaceutical formulation of the medicinal product, on the nature of exact viral infection and exact condition to be treated. In general, in case of homeopathic formulation, prophylactic use would require less frequent intake (1-3 times daily); in an acute condition, treatment can be started with more frequent intake (up to 7-10 times daily), with subsequent tapering down to 3-4 times daily until complete resolution of the symptoms. Selection of the best dosage schedule lies within the limits of due experimentation performed in the course of drug development.

INDUSTRIAL APPLICATION

The present invention can be applied to manufacture effective and safe pharmaceutical compositions and medicaments for prevention and treatment of a wide range of medical conditions in humans and in veterinary practice.

The invention claimed is:

1. An enteral pharmaceutical composition for the treatment of a disease caused by an influenza virus in humans, said composition containing an effective therapeutic amount or formulation of full antibodies or antigen-binding fragments of antibodies specific for the toll-like receptor 3 peptide of SEQ ID NO: 1, wherein the composition comprising said full antibodies or antigen-binding fragments of antibodies is able to reduce severity and duration of a disease caused by an influenza virus.

2. The pharmaceutical composition as defined in claim 1 for use as a medicament intended for oral administration.

3. The pharmaceutical composition of claim 1, wherein said antibody fragments are Fab, F(ab)2 fragments, or antibody monomers containing one heavy and one light immunoglobulin chain.

4. The pharmaceutical composition of claim 1, wherein said antibody fragments are obtained by treating whole antibodies with an endopeptidase selected from the group consisting of papain, pepsin, and ficin.

5. The pharmaceutical composition of claim 1, wherein said antibodies or antibody fragments are obtained by the methods of genetic engineering.

6. The pharmaceutical composition of claim 1, containing an effective therapeutic amount or formulation of full antibodies or antigen-binding fragments of antibodies specific for the toll-like receptor 3 peptide of SEQ ID NO: 1, wherein the composition is effective for modulating the antiviral host response and reducing the severity and duration of viral infections.

7. An enteral homeopathically potentised pharmaceutical composition for the treatment of a disease caused by an influenza virus in humans, said composition containing an effective homeopathically potentised therapeutic amount or formulation of full antibodies or antigen-binding fragments of antibodies for the toll-like receptor 3 peptide of SEQ ID NO: 1, wherein the composition comprising said full antibodies or antigen-binding fragments of antibodies is able to reduce severity and duration of a disease caused by an influenza virus.

8. The pharmaceutical composition of claim 7, wherein the full antibodies or antigen-binding fragments of antibodies specific for the toll-like receptor 3 peptide of SEQ ID NO: 1 are present in the formulation as a mixture of several homeopathic dilutions designed for oral administration.

9. The pharmaceutical composition of claim 7, wherein the full antibodies or antigen-binding fragments of antibodies specific for the toll-like receptor 3 peptide of SEQ ID NO: 1 are homeopathically potentised with the use of technology comprising multiple cycles of consecutive dilution and vertical shaking by the methods of manufacturing described in German Homeopathic Pharmacopoeia, Translation of the 5th Supplement—1991- to the 1978 edition, Deutscher Apotheker-Verlag Stuttgart, pp. 27-82.

10. A homeopathic oral pharmaceutical composition for the treatment of a disease caused by an influenza virus in humans, said composition containing an effective therapeutic amount or formulation of full antibodies or antigen-binding fragments of full antibodies specific for the toll-like receptor 3 peptide of SEQ ID NO: 1, wherein the composition comprising said full antibodies or antigen-binding fragments of antibodies is able to reduce severity and duration of a disease caused by an influenza virus.

11. An oral pharmaceutical dosage form for the treatment of a disease caused by an influenza virus in humans, said composition containing an effective therapeutic amount or formulation of full antibodies or antigen-binding fragments of antibodies specific for the toll-like receptor 3 peptide of SEQ ID NO: 1, wherein the formulation comprising said full antibodies or antigen-binding fragments of antibodies is able to reduce severity and duration of a disease caused by an influenza virus.

12. A process of preparing an enteral pharmaceutical composition comprising full antibodies or antigen-binding fragments of antibodies specific for the toll-like receptor 3 peptide of SEQ ID NO: 1 for the treatment of a disease caused by an influenza virus in humans, wherein the composition comprising said full antibodies or antigen-binding fragments of antibodies is able to reduce severity and duration of a disease caused by an influenza virus, said process comprising the step of adding one or more excipients to said full antibodies or antigen-binding fragments to prepare a liquid or solid dosage pharmaceutical form.

13. A method for preparation of an enteral homeopathically potentised pharmaceutical composition for the treatment of a disease caused by an influenza virus in humans, said composition containing an effective homeopathically potentised therapeutic amount or formulation of full antibodies or antigen-binding fragments of antibodies specific for the toll-like receptor 3 peptide of SEQ ID NO: 1, said method comprising at least the following steps:
   a) Synthesis of the peptide sequence of toll-like receptor 3 as set forth in Seq ID NO:1,
   b) Coupling said peptide with Keyhole Limpet Hemocyanin (KLH) to yield a peptide-KLH conjugate,
   c) Immunization of a laboratory animal with said peptide-KLH conjugate,
   d) Collection and preliminary purification of immune sera from said laboratory animal, said sera containing full antibodies specific for the toll-like receptor 3 peptide of SEQ ID NO: 1
   e) Affinity purification of said immune sera containing full antibodies specific for the toll-like receptor 3 peptide of SEQ ID NO: 1 on Protein A or G or Immunoglobulin binding ligand,
   f) Purification of the sample resulting from step e) on KLH-BrCN-Sepharose or affinity purification on a toll-like receptor 3 peptide sequence as set forth in Seq ID NO:1 to yield full antibodies specific for the toll-like receptor 3 peptide of SEQ ID NO: 1
   g) Homeopathic potentisation of said purified full antibodies of step f), and
   h) Preparation of either a liquid or solid dosage form of the homeopathically potentised full antibodies produced by step (g) as the enteral homeopathically potentised pharmaceutical composition containing an effective homeopathically potentised therapeutic amount or formulation of full antibodies or antigen-binding fragments of antibodies specific for the toll-like receptor 3 peptide of SEQ ID NO: 1.

14. A method for preparation of an enteral homeopathically potentised pharmaceutical composition for the treatment of a disease caused by an influenza virus in humans, said composition containing an effective homeopathically potentised therapeutic amount or formulation of full antibodies or antigen-binding fragments of antibodies specific for the toll-like receptor 3 peptide of SEQ ID NO: 1, said method comprising at least the following steps:
   a) Synthesis of the peptide sequence of toll-like receptor 3 as set forth in Seq ID NO:1,
   b) Coupling said peptide with Keyhole Limpet Hemocyanin (KLH) to yield a peptide-KLH conjugate,
   c) Immunization of a laboratory animal with said peptide-KLH conjugate,
   d) Collection and preliminary purification of immune sera from said laboratory animal, said sera containing full antibodies specific for the toll-like receptor 3 peptide of SEQ ID NO: 1,
   e) Affinity purification of said immune sera containing full antibodies specific for the toll-like receptor 3 peptide of SEQ ID NO: 1 on Protein A or G or Immunoglobulin binding ligand,
   f) Purification of the sample resulting from step e) on KLH-BrCN-Sepharose or affinity purification on a toll-like receptor 3 peptide sequence as set forth in Seq ID NO:1,
   g) Ion exchange purification of the sample resulting from step f) to yield full antibodies specific for the toll-like receptor 3 peptide of SEQ ID NO: 1,
   h) Homeopathic potentisation of said purified full antibodies of step g) according to technology described in German Homeopathic Pharmacopoeia, Translation of the 5th Supplement—1991- to the 1978 edition, Deutscher Apotheker-Verlag Stuttgart, pp. 27-82, and
   i) Preparation of either a liquid or solid dosage form of the homeopathically potentised full antibodies produced by step (h) as the enteral homeopathically potentised pharmaceutical composition containing an effective homeopathically potentised therapeutic amount or formulation of full antibodies or antigen-binding fragments of antibodies specific for the toll-like receptor 3 peptide of SEQ ID NO: 1.

15. A method for preparation of an enteral homeopathically potentised pharmaceutical composition for the treatment of a disease caused by an influenza virus in humans, said composition containing an effective homeopathically potentised therapeutic amount or formulation of full antibodies or antigen-binding fragments of antibodies specific for the toll-like receptor 3 peptide of SEQ ID NO: 1, said method comprising at least the following steps:
   a) Synthesis of the peptide sequence of toll-like receptor 3 as set forth in Seq ID NO:1,
   b) Coupling said peptide with Keyhole Limpet Hemocyanin (KLH) to yield a peptide-KLH conjugate,
   c) Immunization of a laboratory animal with said peptide-KLH conjugate,
   d) Collection and preliminary purification of immune sera from said laboratory animal, said sera containing full antibodies specific for the toll-like receptor 3 peptide of SEQ ID NO: 1,
   e) Affinity purification of said immune sera containing full antibodies specific for the toll-like receptor 3 peptide of SEQ ID NO: 1 on Protein A or G or Immunoglobulin binding ligand,
   f) Purification of the sample resulting from step e) on KLH-BrCN-Sepharose or affinity purification on a toll-like receptor 3 peptide sequence as set forth in Seq ID NO:1,
   g) Ion exchange purification of the sample resulting from step f) to yield full antibodies specific to the peptide sequence of toll-like receptor 3 set forth in Seq ID NO:1,
   h) fragmentation of said full antibodies specific to the peptide sequence of toll-like receptor 3 set forth in Seq ID NO:1 to yield antigen-binding fragments of antibodies specific for the toll-like receptor 3 peptide of SEQ ID NO: 1,
   i) Homeopathic potentisation of said full antibodies of step g) or said antigen binding fragments of antibodies of step h) according to technology described in German Homeopathic Pharmacopoeia, Translation of the 5th Supplement—1991- to the 1978 edition, Deutscher Apotheker-Verlag Stuttgart, pp. 27-82, and
   j) Preparation of either a liquid or solid dosage form of the homeopathically potentised full antibodies or antigen binding fragments produced by step h) as the enteral homeopathically potentised pharmaceutical composition containing an effective homeopathically potentised therapeutic amount or formulation of full antibodies or antigen-binding fragments of antibodies specific for the toll-like receptor 3 peptide of SEQ ID NO: 1.

* * * * *